United States Patent
Nardini

[19]
[11] Patent Number: 6,136,277
[45] Date of Patent: Oct. 24, 2000

[54] FRAGRANCE DISPERSION SYSTEM

[76] Inventor: Joseph Nardini, 888 Derry Dr., Toms River, N.J. 08753

[21] Appl. No.: 09/132,976

[22] Filed: Aug. 12, 1998

[51] Int. Cl.[7] ..................................................... A62B 7/08
[52] U.S. Cl. ......................... 422/124; 360/132; 422/110; 422/122; 422/123
[58] Field of Search ................... 422/124, 110, 422/122, 123; 360/132

[56] References Cited

U.S. PATENT DOCUMENTS

| | | | |
|---|---|---|---|
| 2,144,190 | 1/1939 | Merz | 272/9 |
| 2,608,436 | 8/1952 | Baughman | 299/20 |
| 3,441,353 | 4/1969 | Claff | 401/132 |
| 4,603,030 | 7/1986 | McCarthy | 422/4 |
| 4,629,604 | 12/1986 | Spector | 422/124 |
| 4,905,112 | 2/1990 | Rhodes | 360/132 |
| 5,591,409 | 1/1997 | Watkins | 422/110 |
| 5,724,256 | 3/1998 | Lee et al. | 364/502 |

*Primary Examiner*—Krisanne Thornton
*Attorney, Agent, or Firm*—Joseph N. Breaux

[57] ABSTRACT

A fragrance dispersion system that includes a multi-scent scent dispensing assembly having multiple electronically gateable scent dispensing ports for dispensing a scent in response to a control signal. The gateable scent dispensing ports are controllable through an interface cord by a broadcast signal such that key scents are released as desired. The multi-scent scent dispensing assembly also includes multiple separate scent reservoirs each in connection with a separate electronically gateable scent dispensing port that is interfaceable with audio-video equipment to dispense scents from one or more of the separate scent reservoirs in response to signals transmitted along with the audio or video program. The scent is ejected onto an absorbent scent mixing tape for mixing more than one scent.

1 Claim, 3 Drawing Sheets

6,136,277

FRAGRANCE DISPERSION SYSTEM

TECHNICAL FIELD

The present invention relates to scent dispersal devices and system and more particularly to a scent dispersal system that includes a multi-port scent cassette having a multi-scent scent dispensing assembly that includes multiple separate scent reservoirs each in connection with a separate electronically gateable scent dispensing port that is interfaceable with audio or video equipment to dispense scents from the separate scent reservoirs in response to signals transmitted along with the audio or video program; the scent dispersal system including a blower assembly and a multi-port scent cassette; the blower assembly including a cover grate, a scent cassette scent mixing tape feed reel resistance nut, a scent cassette scent mixing tape take-up reel drive nut, a blower fan, a cassette drive on/off button, a fan on/off button, a scent cassette interface connector jack, and scent cassette controller interface cord; the multi-port scent cassette including a cassette housing, a length of absorbent scent cassette scent mixing tape connected between a scent mixing tape feed reel and a scent mixing tape take-up reel, and a multi-scent scent dispensing assembly; the multi-scent scent dispensing assembly including multiple separate scent reservoirs each in connection with a separate electronically gateable scent dispensing port that is positioned adjacent to a section of the scent mixing tape such that a liquid scent is ejected from each separate electronically gateable scent dispensing port along a trajectory striking the scent mixing tape; the scent cassette scent mixing tape take-up reel drive nut being controllable through the scent cassette controller interface cord to move an unused section of scent mixing tape in position with respect to the multiple separate electronically gateable scent dispensing ports when a new scent is to be dispersed.

BACKGROUND ART

Television and radio excite the hearing and, in the case of television, the visual senses of the audience. It would add a greater dimensionality to the radio and television experience to have a fragrance dispersal system that could be controlled by the television or radio broadcast signal such that key scents are released as desired. For instance, the smell of fresh brewed coffee could be released during a coffee commercial to provide a olfactory stimulus along with the conventional audio and/or video message.

GENERAL SUMMARY DISCUSSION OF INVENTION

It is thus an object of the invention to provide a fragrance dispersion system that includes a multi-scent scent dispensing assembly that includes multiple electronically gateable scent dispensing ports for dispensing a scent in response to a control signal.

It is a further object of the invention to provide a fragrance dispersion system that is controllable through an interface cord by a broadcast signal such that key scents are released as desired.

It is a still further object of the invention to provide a fragrance dispersion system that includes a multi-port scent cassette having a multi-scent scent dispensing assembly that includes multiple separate scent reservoirs each in connection with a separate electronically gateable scent dispensing port that is interfaceable with audio or video equipment to dispense scents from the separate scent reservoirs in response to signals transmitted along with the audio or video program; the scent dispersal system including a blower assembly and a multi-port scent cassette; the blower assembly including a cover grate, a scent cassette scent mixing tape feed reel resistance nut, a scent cassette scent mixing tape take-up reel drive nut, a blower fan, a cassette drive on/off button, a fan on/off button, a scent cassette interface connector jack, and scent cassette controller interface cord; the multi-port scent cassette including a cassette housing, a length of absorbent scent cassette scent mixing tape connected between a scent mixing tape feed reel and a scent mixing tape take-up reel, and a multi-scent scent dispensing assembly; the multi-scent scent dispensing assembly including multiple separate scent reservoirs each in connection with a separate electronically gateable scent dispensing port that is positioned adjacent to a section of the scent mixing tape such that a liquid scent is ejected from each separate electronically gateable scent dispensing port along a trajectory striking the scent mixing tape; the scent cassette scent mixing tape take-up reel drive nut being controllable through the scent cassette controller interface cord to move an unused section of scent mixing tape in position with respect to the multiple separate electronically gateable scent dispensing ports when a new scent is to be dispersed.

It is a still further object of the invention to provide a fragrance dispersion system that accomplishes some or all of the above objects in combination.

Accordingly, a fragrance dispersion system is provided. The fragrance dispersion system includes a multi-port scent cassette having a multi-scent scent dispensing assembly that includes multiple separate scent reservoirs containing a liquid scent agent, each in connection with a separate electronically gateable scent dispensing port that is controllably interfaceable with audio-video equipment to dispense scents from the separate scent reservoirs in response to signals transmitted along with an audio-video program; the scent dispersal system including a blower assembly and a multi-port scent cassette; the blower assembly including a cover grate, a scent cassette scent mixing tape feed reel resistance nut, a scent cassette scent mixing tape take-up reel drive nut, a blower fan, a cassette drive on/off button, a fan on/off button, a scent cassette interface connector jack, and scent cassette controller interface cord; the multi-port scent cassette including a cassette housing, a length of absorbent scent cassette scent mixing tape connected between a scent mixing tape feed reel and a scent mixing tape take-up reel, and a multi-scent scent dispensing assembly; the multi-scent scent dispensing assembly including multiple separate scent reservoirs each in connection with a separate electronically gateable scent dispensing port that is positioned adjacent to a section of the scent mixing tape such that a liquid scent is ejected from each separate electronically gateable scent dispensing port along a trajectory striking the scent mixing tape; the scent cassette scent mixing tape take-up reel drive nut being controllable through the scent cassette controller interface cord to move an unused section of scent mixing tape in position with respect to the multiple separate electronically gateable scent dispensing ports when a new scent is to be dispersed.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
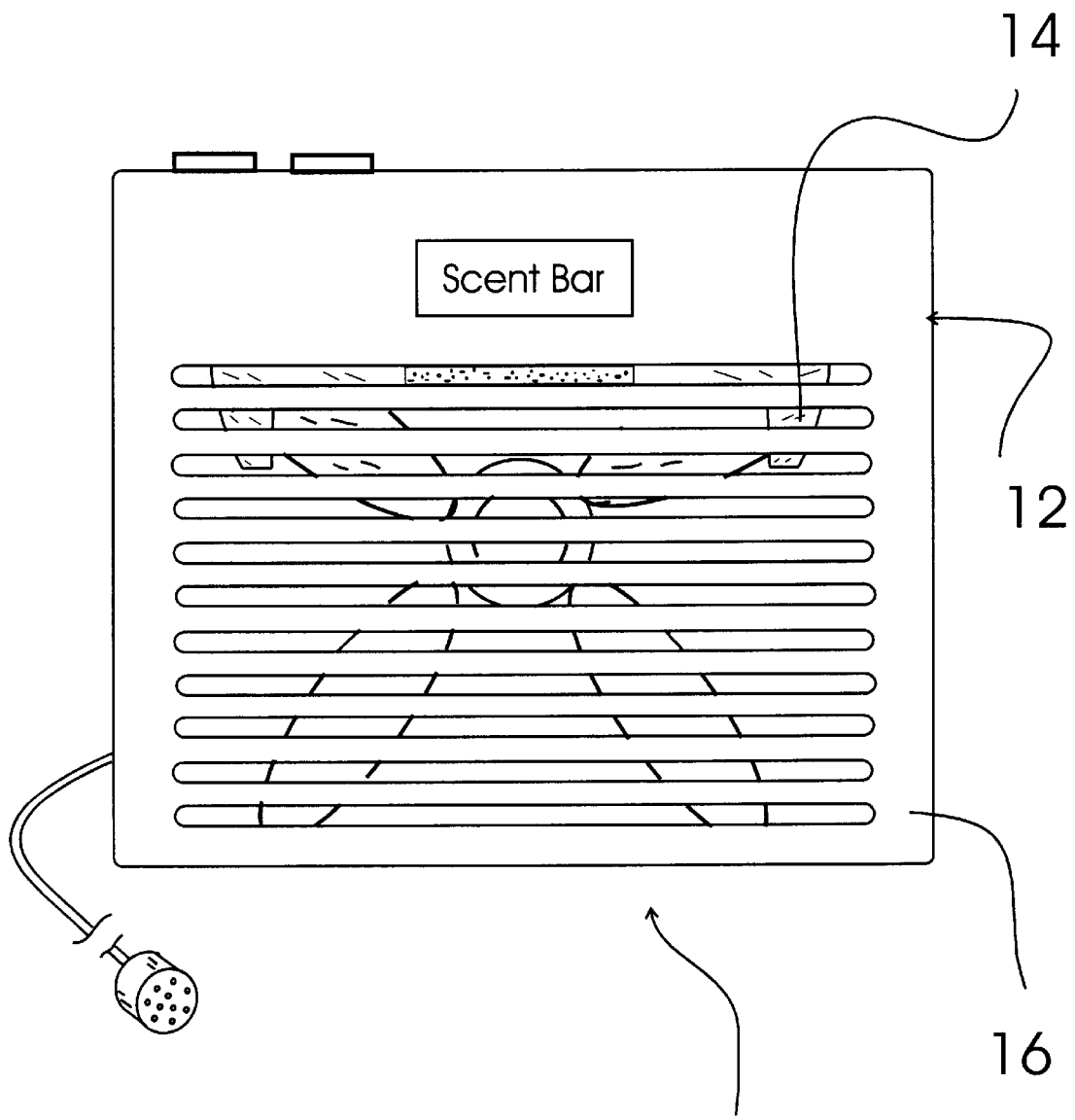
FIG. 1 is a front plan view of an exemplary embodiment of the scent dispersion system of the present invention showing the front grate of the blower assembly, the multi-port scent cassette, and the scent cassette controller interface cord.
Figure 2:
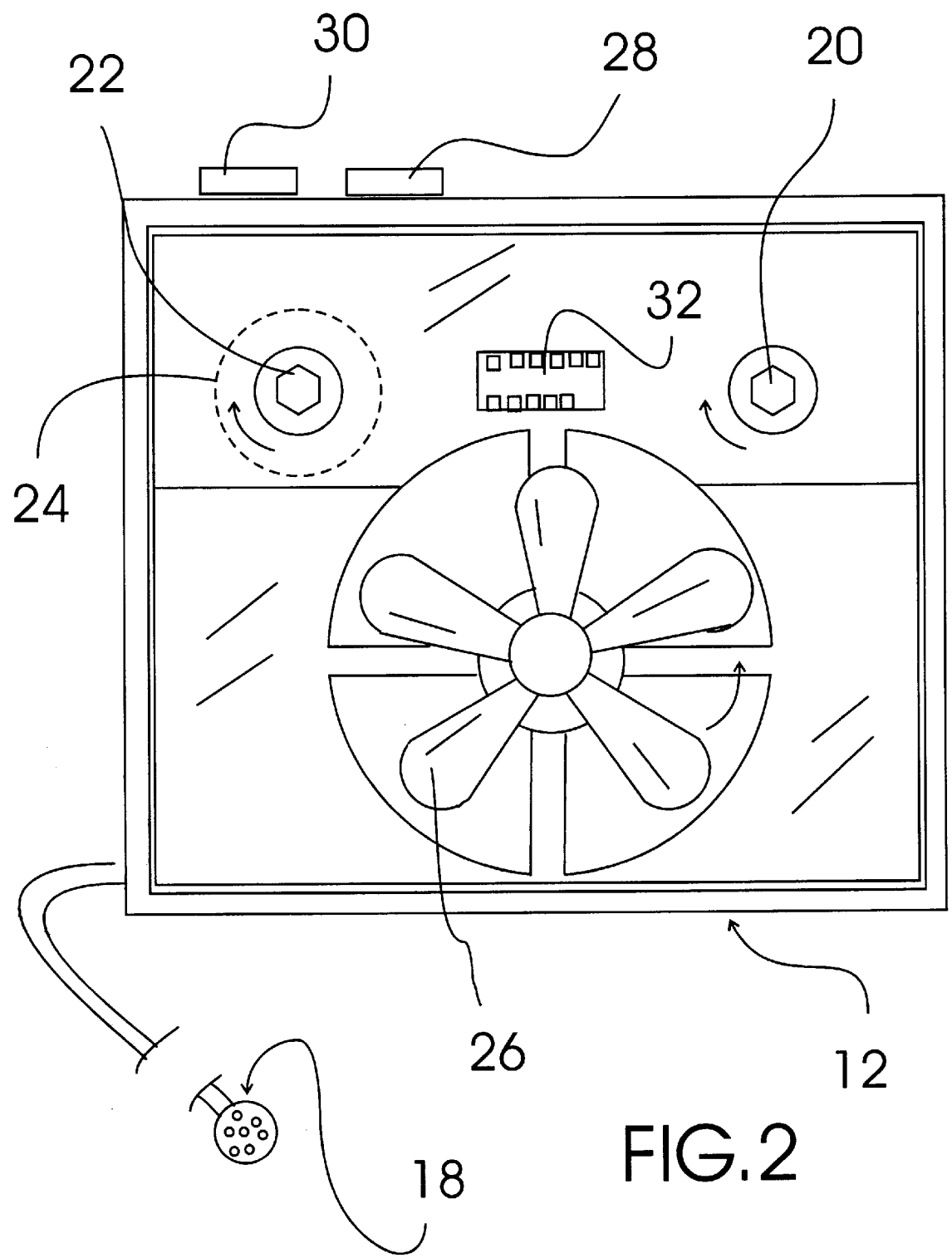
FIG. 2 is a front plan view of the blower assembly with the front grate and scent cassette removed to show the scent cassette feed reel resistance nut, the scent cassette scent mixing tape take-up reel drive nut, the blower fan, the cassette drive on/off button, the fan on/off button, and the scent cassette interface connector jack.
Figure 3:
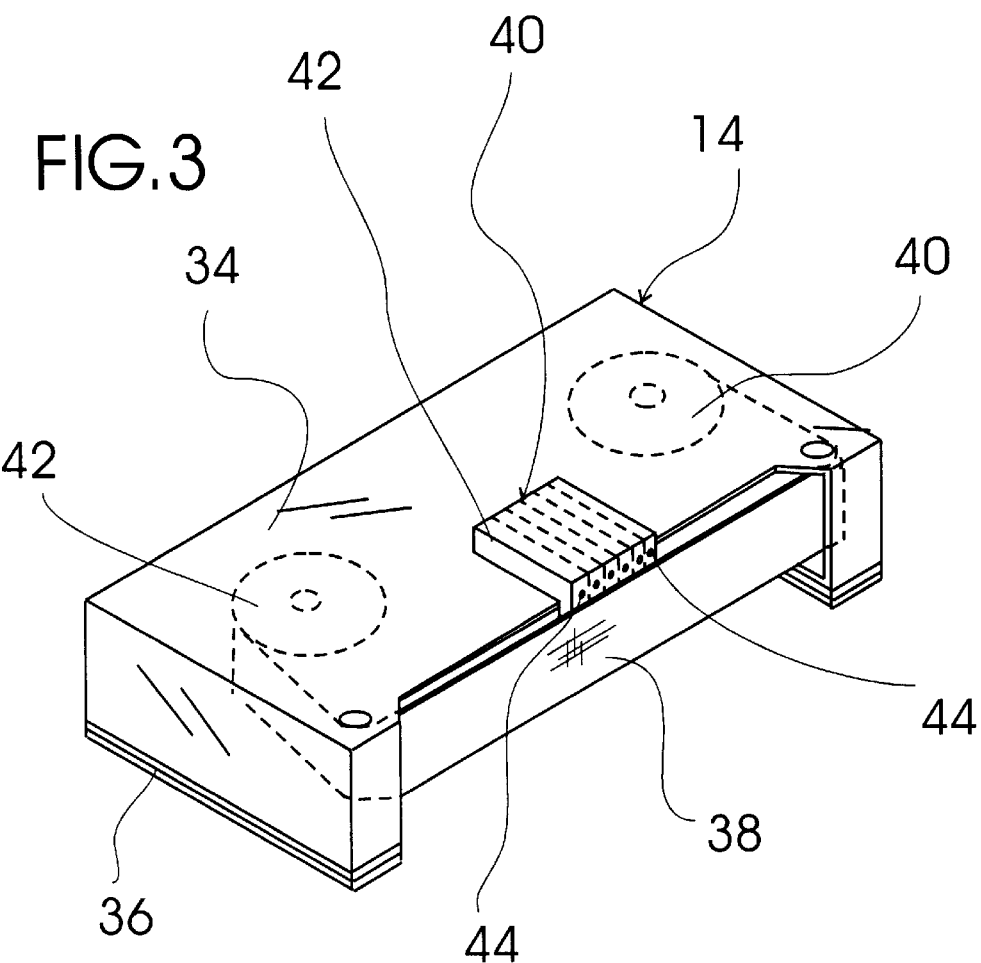
FIG. 3 is a perspective view of an exemplary embodiment of the multi-port scent cassette showing the cassette housing with the restickable adhesive back, the absorbent scent cassette scent mixing tape, the tape feed reel, the tape take-up reel, and the multi-scent scent dispensing assembly including multiple separate scent reservoirs each in connection with a separate electronically gateable scent dispensing ports.

FIG. 1 shows an exemplary embodiment of the scent dispersion system of the present invention generally designated by the numeral 10. Scent dispersion system 10 includes a blower assembly, generally designated 12; and a multi-port scent cassette generally designated 14. Blower assembly 12 has a removable grate 16, and, with reference to FIG. 2, a scent controller interface cord 18, a scent cassette feed reel resistance nut 20, a scent cassette scent mixing tape take-up reel drive nut 22, a take-up reel drive motor 24, a blower fan 26, a cassette drive on/off button 20, a fan on/off button 30, and a scent cassette interface connector jack 32. Scent cassette interface jack 32 is electrically coupled to scent controller interface cord 18 to provide a control signal pathway between the control output of an audio/video component and, referring now to FIG. 3, multi-port scent cassette 14.

Figure 4:
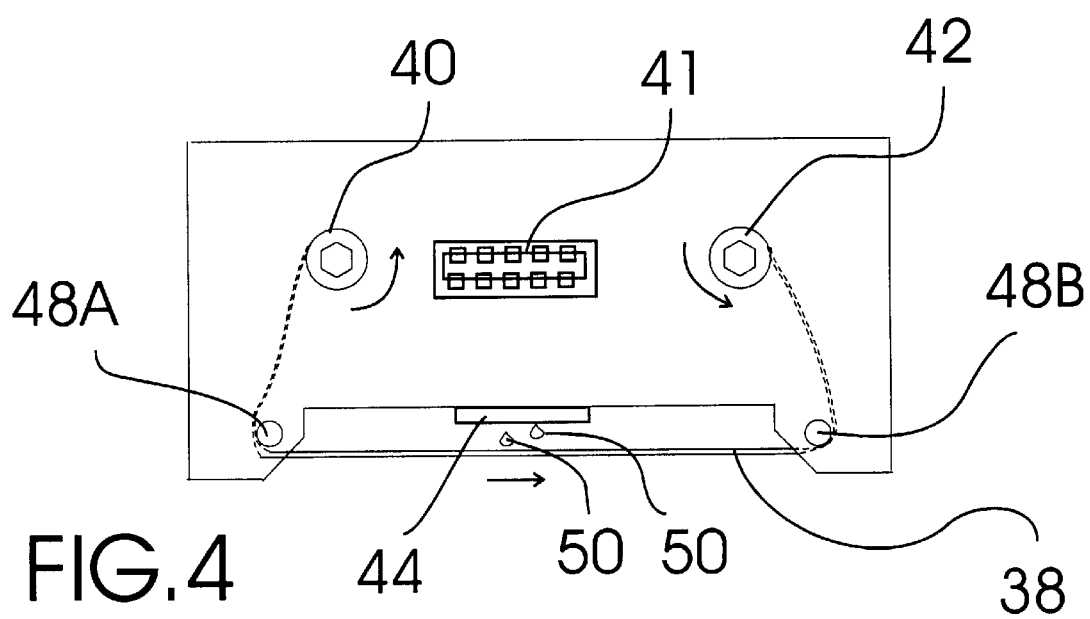
FIG. 4 is a back side plan view of the multi-port scent cassette of FIG. 3 showing liquid scent from two of the separate electronically gateable scent dispensing ports being ejected onto a section of the absorbent scent mixing tape and the raised scent cassette interface connector plug that interconnects with the scent cassette interface connector jack of the blower assembly when the multi-port scent cassette is installed therein.

Multi-port scent cassette 14 includes a cassette housing 34 having a restickable adhesive back 36, a length of absorbent cotton scent cassette scent mixing tape 38, a tape feed reel 40 (in dashed lines), a tape take-up reel 42 (in dashed lines), a multi-scent scent dispensing assembly, generally designated 40, and a raised scent cassette interface connector plug 41 that interconnects with scent cassette interface connector jack 32 (FIG. 2) of blower assembly 12 (FIG. 2) when multi-port scent cassette 14 is installed therein. Multi-scent scent dispensing assembly 40 includes multiple, separate scent reservoirs 42 (in dashed lines) each in connection with a separate electronically gateable scent dispensing port 44. Scent mixing tape 38 is initially attached between feed reel 40 and take-up reel 42 and, referring now to FIG. 4, is fed between two tape guides 48a,48b positioned to guide scent mixing tape 38 in the line of trajectory of the electronically gateable scent dispensing ports 44 (see also FIG. 3).

Generally referring to FIGS. 1–4, in use, operations of drive motor 24 and electronically gateable scent dispensing ports 44 are controlled by an outside controller preferably provided on an audio/video component. Liquid scent agents 50 are ejected onto a section of scent mixing tape 38, and thereafter dispersed into the room by fan 26, in response to control signals provided to the electronically gateable scent dispensing ports 44. When it is desired to eliminate the scent, drive motor 24 is operated until the section of scent mixing tape 38 with the scent is wound onto take-up reel 42 and prevented from further emitting scent into the surrounding area. In this manner programming signals control the dispersion of desired scents 50 along with an audio/video program to enhance the audio/video program.

It can be seen from the preceding description that a fragrance dispersion system has been provided that includes a multi-scent scent dispensing assembly having multiple electronically gateable scent dispensing ports for dispensing a scent in response to a control signal; that is controllable through an interface cord by a broadcast signal such that key scents are released as desired; and that includes a multi-port scent cassette having a multi-scent scent dispensing assembly that includes multiple separate scent reservoirs each in connection with a separate electronically gateable scent dispensing port that is interfaceable with audio or video equipment to dispense scents from the separate scent reservoirs in response to signals transmitted along with the audio or video program; the scent dispersal system including a blower assembly and a multi-port scent cassette; the blower assembly including a cover grate, a scent cassette scent mixing tape feed reel resistance nut, a scent cassette scent mixing tape take-up reel drive nut, a blower fan, a cassette drive on/off button, a fan on/off button, a scent cassette interface connector jack, and scent cassette controller interface cord; the multi-port scent cassette including a cassette housing, a length of absorbent scent cassette scent mixing tape connected between a scent mixing tape feed reel and a scent mixing tape take-up reel, and a multi-scent scent dispensing assembly; the multi-scent scent dispensing assembly including multiple separate scent reservoirs each in connection with a separate electronically gateable scent dispensing port that is positioned adjacent to a section of the scent mixing tape such that a liquid scent is ejected from each separate electronically gateable scent dispensing port along a trajectory striking the scent mixing tape; the scent cassette scent mixing tape take-up reel drive nut being controllable through the scent cassette controller interface cord to move an unused section of scent mixing tape in position with respect to the multiple separate electronically gateable scent dispensing ports when a new scent is to be dispersed.

It is noted that the embodiment of the fragrance dispersion system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A fragrance dispersion system comprising:

a blower assembly; and a multi-port scent cassette;

said blower assembly including a cover grate, a scent cassette scent mixing tape feed reel resistance nut, a scent cassette scent mixing tape take-up reel drive nut, a blower fan, a drive motor in driving connection with said take-up reel drive nut, a cassette drive on/off button in controlling connection with said drive motor, a fan on/off button in controlling connection with said blower fan, a scent cassette interface connector jack, and scent cassette controller interface cord in electrical connection with aid scent cassette interface connector jack;

said multi-port scent cassette including a cassette housing, a length of absorbent scent cassette scent mixing tape connected between a scent mixing tape feed reel that is mounted on said feed reel resistance nut and a scent mixing tape take-up reel that is mountable on said take-up reel drive nut, and a multi-scent scent dispensing assembly;

said multi-scent scent dispensing assembly including a raised scent cassette interface connector plug that interconnects with said scent cassette interface connector jack of said blower assembly when said multi-port scent cassette is installed with said scent mixing tape feed reel is mounted on said feed reel resistance nut and said scent mixing tape take-up reel is mountable on said take-up reel drive nut, multiple separate scent reservoirs each filled with a quantity of liquid scent and in connection with a separate electronically gateable scent dispensing port that is positioned adjacent to a section of said scent mixing tape such that said liquid scent is ejected from each separate electronically gateable scent dispensing port along a trajectory striking said scent mixing tape;

said drive motor driving said scent cassette scent mixing tape take-up reel drive nut being controllable through said scent cassette controller interface cord to move an unused section of scent mixing tape in position with respect to said multiple separate electronically gateable scent dispensing ports when a new scent is to be dispersed.

* * * * *